United States Patent
Schneider (10) Patent No.: US 9,763,981 B2
(45) Date of Patent: *Sep. 19, 2017

(54) METHOD FOR PRODUCING AUTOLOGOUS PROTEINS

(71) Applicant: ARTHROGEN GMBH, Ringsee (DE)

(72) Inventor: Ulrich Schneider, Ringsee (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/954,244

(22) Filed: Nov. 30, 2015

(65) Prior Publication Data

US 2016/0136239 A1 May 19, 2016

Related U.S. Application Data

(63) Continuation-in-part of application No. 13/806,442, filed as application No. PCT/DE2011/001322 on Jun. 21, 2011, now Pat. No. 9,200,050.

(51) Int. Cl.
| A61K 38/20 | (2006.01) |
| A61K 38/17 | (2006.01) |
| A61K 38/19 | (2006.01) |
| A61K 38/21 | (2006.01) |
| A61K 35/16 | (2015.01) |

(52) U.S. Cl.
CPC .................. *A61K 35/16* (2013.01)

(58) Field of Classification Search
None
See application file for complete search history.

(56) References Cited

FOREIGN PATENT DOCUMENTS

EP    WO99/09051    2/1999

OTHER PUBLICATIONS

Per QVIST; Bay-Jensen, Anne-Christine; Christiansen, Claus; Dam, Erik B; Pastoureau, Philippe; and Karsdal, Morten A., "The disease modifying osteoarthritis drug (DMOAD): Is it in the horizon?", Pharmacological Research, 2008, pp. 1-7, vol. 58, Elsevier Ltd.
Kean, I.R.L.; and Kean W.F., "Clinical pharmacology of gold", Inflammopharmacology, 2008, pp. 112-125, vol. 16, Birkhauser Verlag, Basel.
Green, D.M.; Noble, P.C.; Ahuero, J.S.; and Birdsall, H.H., "Cellular Events Leading to Chondrocyte Death After Cartilage Impact Injury", Arthritis & Rheumatism, 2006, pp. 1509-1517, vol. 54, No. 5, American College of Rheumatology.
Vuolteenaho, K.; Kujala, P.; Moilanen, T.; and Moilanen, E., "Aurothiomalate and hydroxychloroquine inhibit nitric oxide production in chondrocytes and in human osteoarthritic cartilage", Scandinavian Journal Rheumatol, 2005, pp. 475-479, vol. 34, Taylor & Francis on license from Scandinavian Rheumatology Research Foundation.
Dinubile, Mark J., Plasma gelsolin: in search of its raison d'etre. Focus on "Modifications of cellular responses to lysophosphatidic acide and platelet-activating factor by plasma gelsolin", American Journal of Physiology—Cell Physiology, 2007, pp. C1240-C1242, vol. 292, American Physiology Society.
Silacci, P; Mazzolai, L.; Gauci, C.; Stergiopulos, N.; Yin, H.L.; and Hayoz, D., "Gelsolin superfamily proteins: key regulators of cellular functions", Cellular and Molecular Life Sciences, 2004, pp. 2614-2623, vol. 61, Birkhauser Verlag, Basel.
Osborn, Teresia M.; Verdrengh, Magareta; Stossel, Thomas P.; Tarkowski, Andrej; and Bokarewa, Maria, "Decreased levels of the gelsolin plasma isoform in patients with rheumatoid arthritis", Arthritis Research & Therapy, 2008, pp. 1-9, vol. 10, Osborn et al.; licensee BioMed Centeral Ltd.
Suhler, Eric; Lin, Weng; Yin, Helen L.; and Lee, William, "Decreased plasma gelsolin concentrations in acute liver failure, myocardial infarction, septic shock, and myonecrosis", Critical Care Medicine Journal, 1997, pp. 594-598, vol. 25, Issue 4, Williams & Wilkins.
Lee, Po-Shun; Waxman, Aaron B.; Cotich, Kara L.; Chung, Su Wol; Perrella, Mark A.; and Stossel, Thomas P., "Plasma gelsolin is a marker and therapeutic agent in animal sepsis", Critical Care Medicine Journal, 2007, pp. 849-855, vol. 35, No. 3, Lippincott Williams & Wilkins.
Dinubile, Mark J., "Plasma gelsolin as a biomarker of inflammation", Arthritis Research & Therapy, 2008, pp. 1-2, vol. 10, BioMed Central Ltd.
Kellgren, J.H.; and Lawrence, J.S., "Osteo-arthrosis and disk degeneration in an urban population", Annals of Rheumatic Diseases, 1958, pp. 388-397, vol. 17, BMJ Publishing Group Ltd. & European League Against Rheumatism.
Roos, Ewa M.; Roos, Harald P.; Lohmander, L. Stefan; Ekdahl, Charlotte; and Beynonn, Bruce D., "Knee Injury and Osteoarthritis Outcome Score (KOOS)—Development of a Self-Administered Outcome Measure", Journal of Orthopaedic & Sports Physical Therapy, 1998, pp. 88-96, vol. 78, No. 2, Journal of Orthopaedic & Sports Physical Therapy.
Kraus, Virginia B.; Huebner, Janet L.; Frank, Christian; King, Jeffrey B.; Brown, Spencer; Vail, Parker T.; and Guilak, Farshid, "Urea as a Passive Transport Marker for Arthritis Biomarker Studies", Arthritis & Rheumatism, 2002, pp. 420-427, vol. 46, No. 2, American College of Rheumatology, Wiley-Liss, Inc.
Huser, Camille, A.M.; and Davies, M. Elisabeth, "Validation of an In Vitro Single-Impact Load Model of the.Initiation of Osteoarthritis-like Changes in Articular Cartilage", Journal of Orthopaedic Research 2006, pp. 725-732, Orthopaedic Research Society, Wiley Periodicals.

*Primary Examiner* — David Berke-Schlessel (57) ABSTRACT

A method of introducing proteins to a patient is provided for treating a wide variety of diseases. The method includes collecting blood from a patient's vein. Gold particles are mixed into the blood and the combination of blood and gold particles are allowed to incubate to produce a protein enriched serum. After incubation, the gold particles are removed and the protein enriched serum is administered to a patient such as by syringe injection.

8 Claims, 7 Drawing Sheets

Fig. 7

METHOD FOR PRODUCING AUTOLOGOUS PROTEINS

RELATED APPLICATIONS

The present application is a continuation-in-part of co-pending U.S. patent application Ser. No. 13/806,442 filed Jan. 21, 2013.

DESCRIPTION

The invention relates to a method for producing at least one therapeutically effective protein or a protein mixture in a container, the container being filled with a body fluid, incubated, and the therapeutically effective protein being formed in the body fluid. The invention also relates to a container for carrying out the method and to drugs containing the thus produced proteins as active ingredient.

Degenerative joint diseases are of great significance in both humans and animals. In the case of humans, arthrosis occurs idiopathically (with known risk factors) in older patients, or can arise as a complication in younger patients owing to post-trauma. However, both forms have the same clinical symptoms, including joint pain and restricted function, and frequently lead to a greatly restricted quality of life for the patient affected. Various causes such as overloading, inappropriate loading, joint instability or else infections lead to mechanical and enzymatic damage of the articular cartilage with apoptosis of the chondrocytes, and also to loss of type II collagen and proteoglycans. Here, there is an imbalance between degeneration and repair. Although cartilage degeneration is at the centre of the pathogenesis, the disease affects not only the cartilage but also the articular capsule and the subchondral bone. In the case of cartilage damage, the degradation products reach the synovial fluid and result in synovitis. In addition, damage to the articular capsule can also directly lead to release of inflammatory mediators and a highly traumatized articular capsule also results in joint instability. In the event of a high and cyclic load, the subchondral bone plate adapts with increased bone density. However, as a result of this sclerosing, the bone becomes stiffer and more brittle. This leads, firstly, to a reduction in the capacity for shock absorption, placing a further load on the overlying cartilage, and, secondly, to shear forces at the transition between subchondral bone plate and mineralized bone. In the case of horses suffering from arthrosis and/or osteoarthritis and/or other joint diseases, increased concentrations of the proinflammatory (inflammation-promoting) cytokines tumour necrosis factor alpha (TNFα), interleukin 1 (IL-1) and interleukin 6 (IL-6) and of prostaglandin E2 (PGE2) and metalloproteinases have been measured in the synovial fluid. In the case of humans suffering from arthrosis, the concentration of the proinflammatory cytokines is also increased in blood and in synovial fluid.

The proinflammatory (inflammation-promoting) cytokines TNFα, IL-1 and IL-6 are secreted by the type B synoviocytes (Synoviocyti secretorii) of the synovial membrane, by inflammatory cells in the synovial membrane and by chondrocytes and stimulate the release of matrix metalloproteinases (MMPs) and aggrecanases and of further inflammatory mediators such as prostaglandins (PGE2) or nitric oxide (NO). Metalloproteinases are enzymes which degrade the matrix of cartilage (including type II collagen, proteoglycans). IL-1 and TNFα also directly inhibit the production of type II collagen.

In most cases, the conventional therapy for degenerative joint diseases consists in symptomatic treatment of the inflammation, i.e. in either systemic or intra-articular inhibition of the inflammation by means of appropriate medicaments. These include the corticosteroids, sometimes in combination with hyaluronic acid, which are administered intra-articularly and used most frequently. In addition, chondroprotective agents are also occasionally administered. However, these medicamentous therapies have numerous adverse effects.

An alternative to the symptomatic therapies (on the basis of non-steroidal and steroidal anti-inflammatories) is formed by the treatments with cytokine inhibitors or chondroprotective agents, which are referred to as "disease-modifying drugs" (Qvist et al. 2008). These also include therapies in which endogenous (autologous) proteins are obtained from the blood of the patient and are readministered to said patient as an individual medicament.

WO 9909051 discloses a method for producing therapeutically effective, autologous (=endogenous) proteins in a body fluid sample previously obtained from the (animal or human) patient and a syringe for carrying out said method. The proteins obtainable in this way that were mentioned are erythropoietin, insulin, interferons, interleukin 4, interleukin 10, soluble tumour necrosis factor receptor and the interleukin-1 receptor antagonist. The proteins are produced and provided in a syringe.

The inner structures of the syringe, including particles arranged in the syringe, more particularly glass beads impregnated with chromium sulphate, are coated with immobilized inductors intended to stimulate the biosynthesis of the desired proteins. In the case of blood as a body fluid sample, immmunoglobulins, more particularly immunoglobulin G, are envisaged as such inductors for stimulating the monocytes contained in the blood to form anti-inflammatory proteins.

The method is carried out by filling and incubating the syringe with a body fluid from a patient. The therapeutically effective protein is formed in the body fluid.

The body fluid enriched in this way can be stored sterile in the syringe and, when required, be directly reintroduced into the patient without further treatment or, for example, after centrifugation and/or sterilizing filtration.

It is an object of the present invention to further develop, or modify, such a method such that the proteins generated are present in significantly higher amounts and that undesired side effects are avoided.

This object is achieved by providing a method of the type mentioned at the outset, in which the container contains gold particles.

The term "container" means hereinafter a closable vessel or a closable reservoir for storing liquids for a particular length of time, wherein the vessel or reservoir is leak-proof with respect to the liquid to be accommodated.

The use of gold as a drug has long been known in medicine. At the end of the 19th century, gold was used in particular as a drug for treating tuberculosis. On account of the false assumption that rheumatoid arthritis is likewise an infectious disease, gold was used as a drug for this condition too. The therapy was successful and was then used over many years up to the present day (Kean and Kean 2008). An in vitro study on human chondrocytes showed that gold compounds (aurothiomalate) inhibit the production of nitric oxide (NO) by the chondrocytes. Nitric oxide mediates the destructive effects of the proinflammatory cytokines IL-1 and TNFα (Green et al. 2006). This leads to reduced collagen and proteoglycan production, to chondrocyte apoptosis and to stimulation of the metalloproteinases (Vuolteenaho et al. 2005).

In the therapeutic approaches known in the prior art, the gold is administered either intramuscularly or per os. However, using these methods of administration and the appropriate gold pharmaceutical, the desired effects known from the in vitro studies are only achieved to some extent.

The combination of gold particles with a human or animal autologous or homologous body fluid, more particularly one's own blood sample, in a closed system, said combination being used for the first time in the method according to the invention, provides, surprisingly, not only (i) a distinctly higher concentration of the desired proteins compared to the previously known method, more particularly the cytokines (in particular IL-1, IL-6, IL-8, IL-10, G-CSF, MCP-1, MIP-1, RANTES, TNF-alpha, GRO-alpha, MCP-3, MIF and IL-1RA) in the case of blood, but also (ii) a better quality of the proteins in question owing to inhibition of physiological protein ageing during the incubation time and also (iii) a significant accumulation of the protein gelsolin. Gelsolin is an actin-binding protein which is ubiquitously present in all animal cells (including human cells) and also extracellularly (e.g. in blood plasma), and which fragments $Ca^{2+}$-dependent actin filaments and prevents repolymerization, and which has/fulfils a key function in the regulation of processes for actin-filament assembly and disassembly. Gelsolin was discovered and identified in cytoplasmic extracts, and its ubiquitous presence and phylogenetic conservation in motile cells suggests its essential role as an intracellular regulatory protein. It was only discovered later that gelsolin also occurs in the blood plasma of mammals and depolymerizes actin there. This so-called plasma gelsolin (pGelsolin, pGS) is an isoform of the cytoplasmic gelsolin (cGelsolin, cGS) and differs structurally therefrom in that it has an additional 23 amino acids at the N-terminal end. The physiological function of plasma gelsolin is still the subject of numerous research work (DiNubriu, 2007 and literature cited therein). Gelsolin regulates important cell functions such as cell motility, phagocytosis, apoptosis and thrombocyte activation (Silacci et al. 2004, Trickey et al. 2004). In the case of humans suffering from rheumatoid arthritis, the plasma concentration of gelsolin is reduced (Osborn et al. 2008). In the case of other diseases involving tissue degeneration and, more particularly, in the case of sepsis, the plasma concentration of gelsolin is reduced too (Suhler et al. 1997, Osborn et al. 2008, Lee et al. 2007). Prior-art knowledge indicates that plasma gelsolin serves as a buffer for absorbing excessive inflammatory reactions of the body (DiNubile 2008).

The proteins produced using the method according to the invention, more particularly gelsolin and cytokines, can (but do not have to) be readministered to the patient together with the other constituents of the liquid situated in the container in a direct manner, i.e. without further manipulation, for example centrifugation, sterilizing filtration or transfer to another container. As a result, contamination of the protein solution is avoided and the risk of infection of the patient during administration of the proteins is minimized.

In a variant according to the invention of the method according to the invention, the gold particles are removed from the body fluid, for example serum, after the in vitro incubation and discarded. The advantage of this is that gold-induced adverse effects during or after the administration of said body fluid, for example said serum, are completely avoided.

In a likewise preferred variant according to the invention of the method according to the invention, both the gold particles and somatic cells (for example, blood cells) and other insoluble aggregates are removed from the body fluid (for example, serum) after the in vitro incubation and discarded. Autologous human body fluids and, more particularly, serums of this kind that are prepared are outstandingly tolerable, and adverse effects are not to be expected.

The gold particles used in the method preferably have a defined structure and/or a defined size. Microparticles and/or nanoparticles having a particle size between 10 nanometres to 500 micrometres are especially suitable.

In the variants of the method according to the invention in which the gold particles are to be removed from the body fluid, for example serum, after the in vitro incubation and to be discarded, preferably gold particles of about 1 μm in size are used in the method, further preferably in an amount of $10^3$-$10^4$ gold particles per 10 ml. For this application, containers (e.g. a syringe) whose capacity is about 10 ml have proved themselves in practice.

In one embodiment which has proved successful in practical use, the gold particles are present in the container in an amount of 0.3 mg per 1 ml of body fluid. Concentrations of from 0.1 to 10 mg per 1 ml are suitable as a matter of principle and envisaged.

The inner structure of the container is preferably free of anticoagulants such as heparin, citrate, EDTA or CPDA, since, as part of the work on which this invention is based, it was found that, surprisingly, fewer proteins are biosynthesized in the presence of such substances than in their absence. Especially in the case of blood as body fluid and heparin as anticoagulant, considerably lower cytokine production was obtained in the presence of heparin, for example as coating of the container inner wall, than in the absence of heparin and other anticoagulants.

A possible container is, in particular, a syringe because it not only can be used as an incubation vessel, but is also suitable, at the same time, as a collection instrument for obtaining the body fluid and/or as an administration instrument for administering the proteins to a patient.

However, another possible container is a sealable pouch because, especially in the case of relatively large volumes, it can be handled and stored more flexibly than a syringe of comparable volume, and because it can be coupled to a syringe in a technically simple and reliable manner, and so filling and emptying can be carried out via said syringe.

The method according to the invention is very particularly suitable for the production (biosynthesis) and accumulation of proteins from blood cells. Therefore, particularly blood, preferably blood serum, is envisaged as body fluid.

Surprisingly, the therapeutically effective protein gelsolin can be produced and accumulated especially effectively, i.e. in significant amounts, using the method according to the invention. Therefore, the method according to the invention is intended especially for obtaining gelsolin.

With respect to the incubation conditions for the container filled with body fluid, it has been shown in practice that an incubation time of from 12 to 72 hours, preferably 24 hours, at a temperature of from 20° C. to 41° C., preferably 37° C., leads to good results.

The aforementioned object is also achieved by providing a container for the in vitro biosynthesis and accumulation (in vitro induction) of therapeutically effective proteins in a body fluid, which is distinguished by the fact that the container contains gold particles and is suitable for collecting, storing and redispensing a body fluid sample, and that it is coupleable with a hollow needle (cannula, injection needle) such that its contents can be injected by means of said hollow needle (cannula, injection needle).

Using said container, it is possible to carry out in particular the above-described protein production method and to utilize the advantages associated therewith. The proteins produced can be brought directly to the desired site of administration by means of the coupleable hollow needle, more particularly introduced into a human or animal body.

The gold particles preferably have a defined structure and/or a defined size. Microparticles and/or nanoparticles (particle size between 10 nanometres and 500 micrometres) are especially suitable. An appropriate amount of gold particles in the container is from 0.1 mg to 10 mg per 1 ml of body fluid, preferably 0.3 mg per 1 ml of body fluid.

The container is preferably a syringe or a pouch. The advantage of the syringe is that it can be used not only as an incubation vessel, but also, at the same time, as a collection instrument for obtaining the body fluid and/or as an administration instrument for administering the proteins to a patient. The advantage of the pouch is that, in the case of relatively large volumes, it can be handled and stored more flexibly than a syringe of comparable volume and can be coupled to a syringe for filling and emptying.

An especially highly suitable container is a commercially available syringe (for example, 5 to 100 ml syringes) of no particular design in its inner cavity. The gold particles (e.g. Gold Microcarriers from BioRad Laboratories, cat. 165-2264) are introduced into the syringe cylinder.

The syringe, more particularly the inner wall of the syringe cylinder and the part of the syringe plunger lying in the cylinder, preferably consists of a plastic, for example polystyrene, polyethylene, polyvinyl chloride, polypropylene (neutral S-Monovettes, Sarstedt) or a similar substance or mixtures thereof.

The container is especially highly suited for the production (biosynthesis) and accumulation of proteins, more particularly gelsolin, from blood cells. Therefore, particularly blood, preferably blood serum, is envisaged as body fluid.

The proteins produced in a body fluid using the method according to the invention can be used as a drug for treating diseases, together with the body fluid and the gold particles or without the gold particles.

The protein-enriched and, more particularly, cytokine-enriched and gelsolin-enriched body fluids, more particularly blood serums, which are produced using the method according to the invention represent an alternative to comparable conventional drug preparations that is safer, can be produced inexpensively and rapidly, and is especially low in adverse effects.

The present invention therefore also provides a protein-enriched body fluid, more particularly a cytokine-enriched and gelsolin-enriched blood serum, for use as a drug or for production of a drug, obtainable by the body fluid, more particularly blood serum, being collected in a container which contains gold particles, preferably gold particles of about 1 μm in size and preferably in an amount of $10^3$-$10^4$ gold particles per 10 ml of container (or 0.3 mg of gold particles having a diameter of 1 μm per 1 ml of blood/container), by this mixture of body fluid, more particularly blood serum, and gold particles being incubated (for example, for 12-72 hours, preferably for 24 hours, and at from 20° C. to 41° C., preferably at 37° C.), and, subsequently, by the gold particles and preferably (i.e. optionally) additionally blood cells and other insoluble constituents being removed from the body fluid, more particularly serum, and discarded (preferably by centrifugation and/or sterilizing filtration).

The invention also provides for the use of autologous or homologous blood and gold particles in combination as a drug or for the production of a drug. In other words: the present invention also provides a substance mixture composed of autologous or homologous blood and gold particles for use as a drug, or a drug comprising the substance mixture composed of autologous or homologous blood and gold particles including the proteins accumulated therein as active-ingredient combination.

The drugs according to the invention allow an especially simple, inexpensive, low-risk and effective treatment.

The described drugs are especially suitable for the treatment of degenerative joint diseases, in particular arthroses and tendinoses. Particularly the drug incubated with gold particles and subsequently depleted of particles is highly suitable and envisaged for the treatment of arthrosis and other diseases associated with tissue degeneration and/or associated with gelsolin deficiency.

One particular embodiment of the drugs according to the invention is distinguished by the body fluid (more particularly blood) incubated with gold particles having, after the incubation, a gelsolin content which is at least double the relevant standard blood value for gelsolin. In the present context, the term "relevant standard blood level for gelsolin" means the medical or veterinary standard value for gelsolin in the blood of that patient group to be treated with the drug. The patient group is characterized in terms of its zoological species and race, sex and age.

This gelsolin-rich drug is envisaged for the treatment of any disease associated with a gelsolin deficiency in the blood of a patient. These include rheumatoid arthritis, osteoarthritis, disc herniation, tendonitis, Alzheimer disease, acute myocardial infarction, diabetes mellitus, myonecrosis, acute liver failure, chronic hepatitis, cirrhosis of varying etiology, pancreatitis, septic shock, wound healing, and brain trauma/infarction.

Moreover, the injection of the gelsolin rich drug to a patient is believed to provide regeneration and assist in the recovery of virtually any type of physical injury, inflammation or degenerative process. It has been found that injuries, inflammations or degenerative processes result in the reduction of gelsolin in the body which can be treated by the administration of the gelsolin rich serum. In addition, the gelsolin rich drug provides anti-inflammatory benefits. Furthermore, through the contact of the patients blood with the gold particles, white blood cells (leukocytes) and monocytes are activated. The monocytes in particular neutralize bacteria and tissue debris which can further treat physical injury, inflammation or degenerative processes.

The injection of the gelsoin rich drug of the present invention is believed to provide stem cell therapy including stem cell activation and differentiation at the site of an injection. For example, important stem cell specific factors like G-CSF (granulocyte-colony stimulating factor) and SCGF-β (hematopoietic stem cell growth factor-beta) are produced to a significantly high degree which can provide beneficial effects for a patient. Accordingly, still many additional diseases are anticipated to be discovered which can be alleviated or treated by introduction of the gelsolin rich drug of the present invention.

The incubated blood-gold mixture can be administered as a whole or in part. If needed, it can be subjected to centrifugation and/or sterilizing filtration prior to administration to the (animal or human) patient in order, for example, to remove cells and cell fragments from the blood and thus, at the same time, to reduce the injection volume as well.

The invention is hereinbelow more particularly elucidated using exemplary embodiments and associated figures.

FIG. 2 shows: the results of a multiplex analysis of the proteins:
GS=gelsolin
IL-4=interleukin-4
IL-10=interleukin-10
IL-13=interleukin-13
IL-1Ra=interleukin-1 receptor antagonist
IL-10=interleukin-1β
TNF-α=tumour necrosis factor alpha
G-CSF=granulocyte-colony stimulating factor
GM-CSF=granulocyte-macrophage colony stimulating factor
IFN-g=interferon gamma
SCGF-β=haematopoietic stem cell growth factor
MIP-1a=macrophage inflammatory protein-1a
MIP-1β=macrophage inflammatory protein-1β
VEGF=vascular endothelial growth factor
IL-18=interleukin-18
MCP-3=macrophage chemotactic protein
SDF-a=stromal derived factor
basic FGF=fibroblast growth factor
GROa=growth-regulated oncogene alpha
in blood samples at time T0 ("T0") and after a 24-hour incubation, without further treatment ("Control") on the one hand, and with treatment either in accordance with WO 9909051 ("StdT") or in accordance with the method according to the invention ("Invention") on the other hand.

EXAMPLE 1

Checking Protein Production in a Blood Sample Following the Method According to the Invention and in a Container According to the Invention by Means of a MID-FTIR Spectroscopy Method and Multiplex Analysis Two 9 ml blood samples from each of 11 different patients (Nos. 1-11) were collected in a container according to the invention, viz. a 9 ml syringe filled beforehand with 2.7 mg of gold particles (having a diameter of 1 µm). An identical amount of blood sample from the same source (patients) was collected in a similar 9 ml syringe without any gold particles as content. The samples were analysed at different times, viz. at time T0 immediately after blood withdrawal and at time T24 after incubation for 24 hours at 37° C.

The samples were analysed by means of Fourier transform infrared spectroscopy in the mid-infrared range (spectral range of from 4000 $cm^{-1}$ to 400 $cm^{-1}$), MID-FTIR spectroscopy for short (e.g. the AquaSpec method from Micro-Biolytics GmbH/Esslingen).

The measurement principle behind Fourier transform infrared spectroscopy is based on the irradiation of a substance with electromagnetic waves, with particular frequency ranges being absorbed. Since infrared radiation is energetically in the range of the vibration levels of molecular bonds, absorption leads to stimulation of vibration of the bonds. This becomes visible in the form of deflections in the measured spectrum (diagram). Since the energies or frequencies required therefor are characteristic of the particular bonds, it is thus also possible to identify materials and clarify structures.

FTIR spectroscopy is suitable especially for the analysis of structural, reaction-induced modifications in a biological macromolecule. Using this method, it is possible to investigate biological systems, more particularly protein-containing aqueous liquids. The sample is neither modified nor destroyed and work can be carried out under native conditions of the biomolecule, i.e. the "actual state" can be measured because neither fixation nor a different kind of sample preparation is required.

Since all molecular constituents of the protein have absorption bands in the infrared spectral range, virtually all regions of a protein can be observed and detailed information about the structure of the protein can be obtained.

The MID-FTIR spectroscopy method allows the automated and reproducible identification and quantification of changes in protein conformation and the determination of protein concentration. Even very low protein concentrations (down to below 0.1 mg/ml) and very small conformational changes can be detected.

When carrying out the method in the context of the present invention, the blood samples with and without gold particles were analysed in the "actual" state in a spectroscopic measurement cell (transmission cell) which was highly precise, biocompatible, and suitable for aqueous samples. Using internal calibrations, the concentration of the dissolved protein and its secondary structure (alpha helix, beta sheet) was determined automatically for each measured sample.

Figure 1:
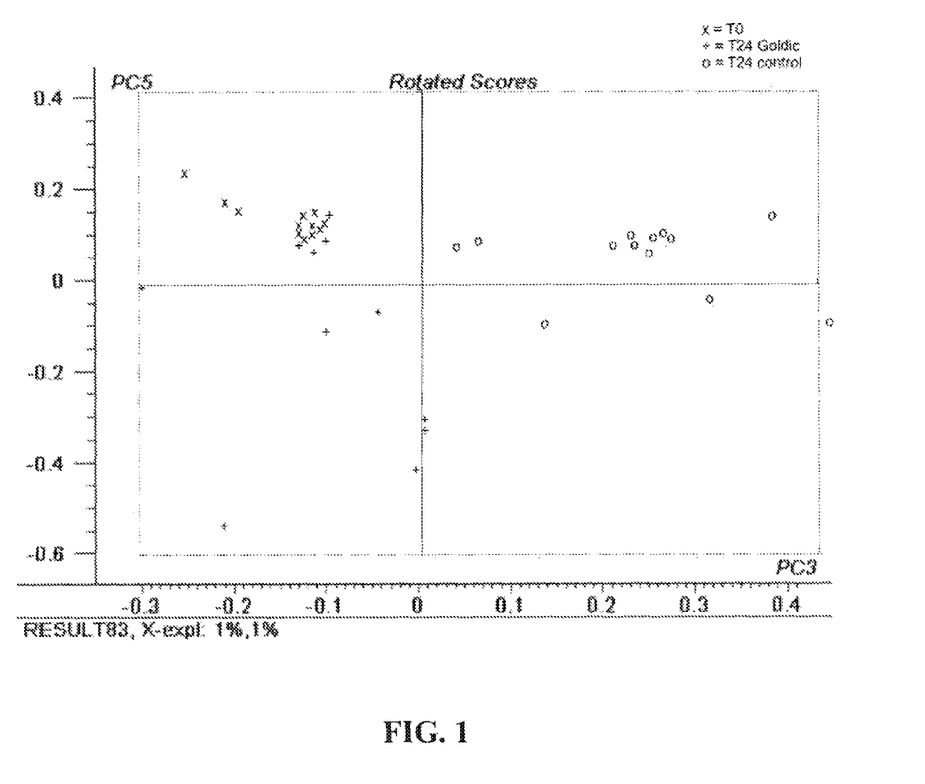
FIG. 1 shows: a MID-FTIR spectroscopic analysis of the protein profile in blood serums of various patients before (T0) and after (T24) carrying out the method according to the invention in comparison with controls. BLUE represents the protein profile for time T0, GREEN shows the protein profile of the samples treated using the method according to the invention at time T24, RED shows the protein profile of the control serums at time T24.

The results of this measurement are depicted graphically in FIG. 1. It shows that the biological behaviour of the samples incubated according to the invention in the presence of gold particles is different from that of the control samples. The measured values of all samples at time T0 are indicated by a blue colour and are predominantly in the upper-left quadrant. The measured values after carrying out the method according to the invention with an incubation period of 24 hours are indicated by a green colour and are predominantly in or near the lower-left quadrant. This indicates that physiological protein ageing during blood incubation is inhibited by the addition of gold. The measured values of the control samples after an incubation period of 24 hours are indicated by a red colour and are predominantly in the upper-right quadrant. This shift to the right indicates ageing of the protein structure.

Using a multiparameter analysis method (synonym: multiplex analysis) on the basis of distinguishably coded microparticles (e.g. the BioPlex™2200 system from BioRad Laboratories, Munich), the following proteins were quantitatively determined at times T0 and T24 in the samples associated with the method according to the invention ("Invention"), the method according to WO 9909051

("StdT") and corresponding controls with no treatment: gelsolin (GS), interleukin-4 (IL-4), interleukin-10 (IL-10), interleukin-13 (IL-13), interleukin-1 receptor antagonist (IL-1Ra), interleukin-1β (IL-1β), tumour necrosis factor alpha (TNF-a), granulocyte-colony stimulating factor (G-CSF), granulocyte-macrophage colony stimulating factor (GM-CSF), interferon gamma (IFN-g), haematopoietic stem cell growth factor (SCGF-β), macrophage inflammatory protein-1 a (MIP-1a), macrophage inflammatory protein-1β (MIP-1β), vascular endothelial growth factor (VEGF), interleukin-18 (IL-18), macrophage chemotactic protein (MCP-3), stromal derived factor (SDF-a), fibroblast growth factor basic (FGF), growth-regulated oncogene alpha (GROa).

These proteins play important roles in tissue degeneration and tissue repair.

Figure 2:
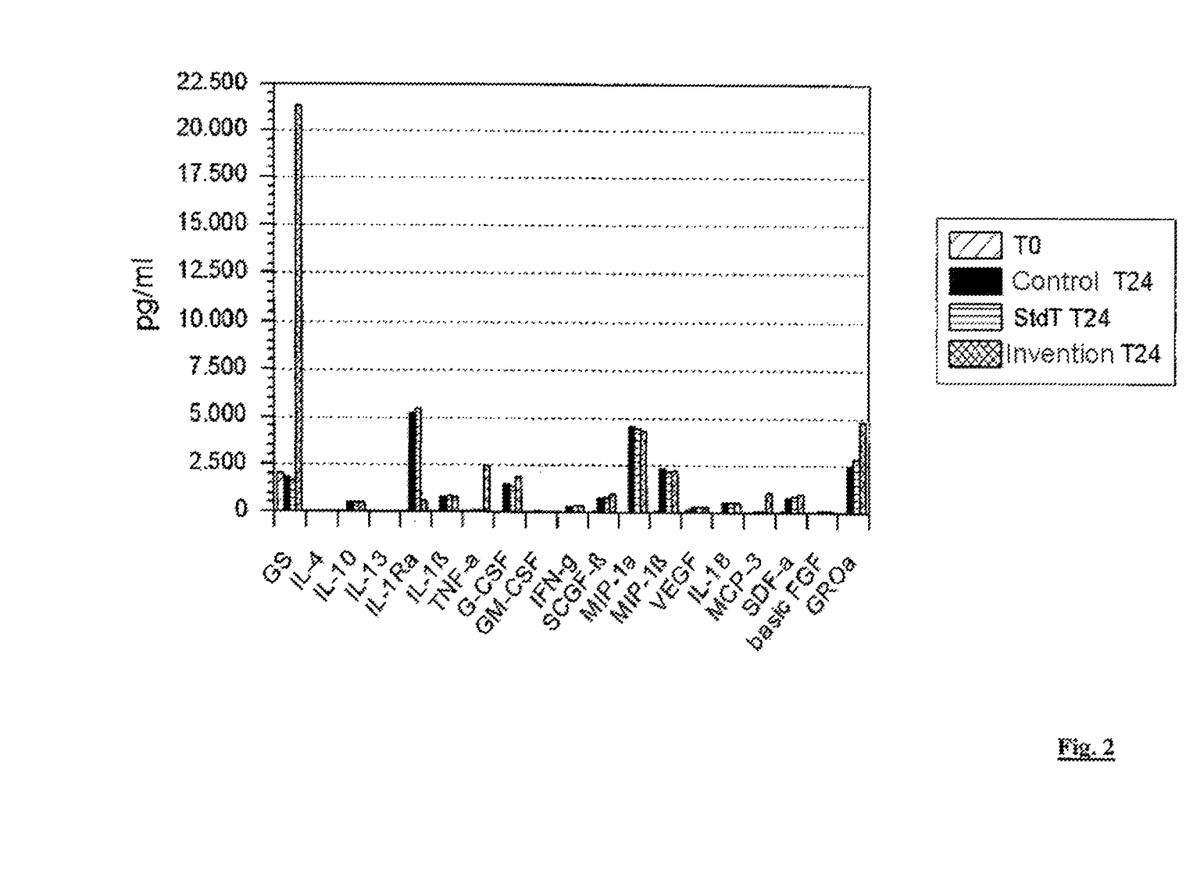

The results of this analysis are shown in table 1 and depicted graphically in FIG. 2.

They show that, for the samples treated according to the invention ("Invention"), a considerable increase in the gelsolin concentration (factor of 10) took place after 24 hours, whereas, for the comparative samples ("Control T24" and "StdT T24"), gelsolin disappearance rather than gelsolin accumulation was found. The concentrations of tumour necrosis factor alpha (TNF-a), macrophage chemotactic protein (MCP-3) and growth-regulated oncogene alpha ("GROa") were also substantially (TNF-a: factor of 30-40; MCP-3: factor of 20-30) or at least distinctly (GROa: factor of 2) higher in the samples treated according to the invention ("Invention") than in the comparative samples ("Control T24" and "StdT T24").

EXAMPLE 2

Drug Efficacy Studies in Animals

A) Soft-Tissue Swelling

As part of a prospective clinical study, 8 horses having pronounced soft-tissue swelling owing to tendinoses (degenerative changes to tendons in the region of attachments to bone) were treated with the drug according to the invention.

To produce the drug, a container according to the invention in the form of a gold particle-containing syringe was filled with blood from the animal in question and incubated for 24 hours at a temperature in the region of 37° C. At the end of the incubation period, the drug was completed in the form of the blood situated in the syringe, containing the proteins synthesized and accumulated during this period, more particularly cytokines and gelsolin, and the gold particles, and could be used directly and immediately.

Since the drug was produced in a syringe, it could be administered to the animal in question by injection without transfer and thus without the risks of contamination and material loss.

For the present study, four such drug-doses were produced at time T0 for each horse, i.e. four gold particle-containing syringes were filled with blood from the animal in question and incubated for 24 hours at a temperature in the region of 37° C.

These drug injections were administered to the respective horse at an interval of one week in each case. The first administration was performed at time T24, and the second, third and fourth ones were performed after week 1, after week 2 and after week 3. The drug-containing syringes for the second, third and fourth administration were stored at minus 20° C. until use.

The swelling state was checked after 1 week, 2 weeks, 3 weeks, 3 months, 6 months and 1 year and rated using a scale of 0-5 (0=no swelling at all, 5=massive swelling).

In all 8 cases, a significant reduction in swelling was found after just 3 weeks. After 6 months and even after one year, all the horses were completely free of swelling. During the treatments, no adverse effects at all were found.

Figure 3:
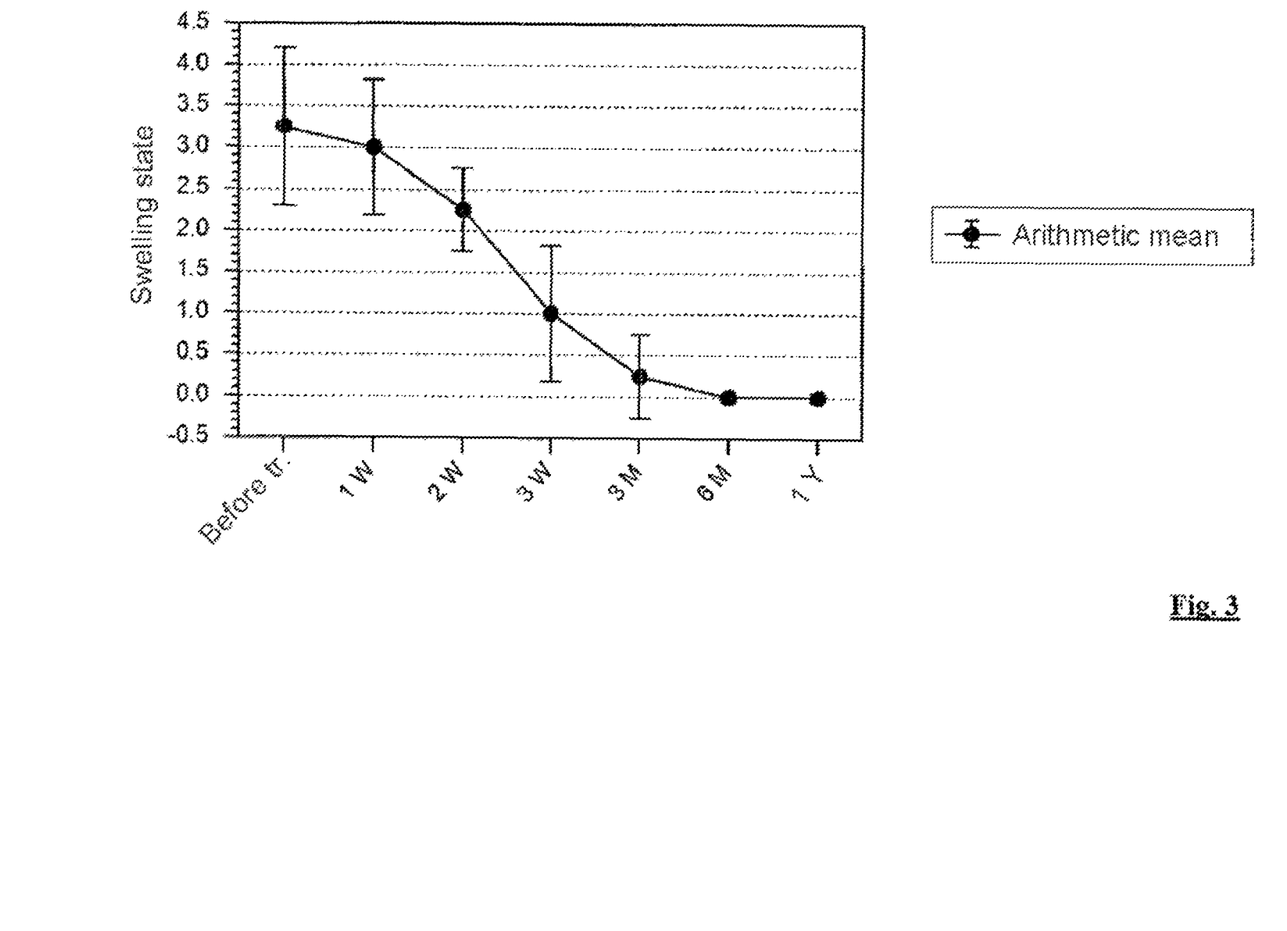
FIG. 3 shows: the graphic representation of the degree of swelling of all horses examined, before and after the treatment according to the invention at the respective re-examination times.

The results of this study are depicted graphically in FIG. 3.

B) Lameness

In a further horse study, 11 horses exhibiting the clinical symptom of lameness (12 extremities affected) were treated with the drug according to the invention. The medical causes of the cases of lameness were, in six of the cases, degenerative cartilage changes (n=6) in/on the joints and, in six of the cases, soft-tissue diseases (n=6).

To produce the drug, for each horse, four containers according to the invention in the form of gold particle-containing syringes were again filled with blood from the animal in question and incubated for 24 hours at a temperature in the region of 37° C. At the end of the incubation period, the drug was completed in principle in the form of the blood situated in the syringe, containing the proteins synthesized and accumulated during this period, more particularly cytokines and gelsolin, and the gold particles. In order to minimize the injection volume, corpuscular fractions were removed by centrifugation for 10 minutes at 5000 rpm in a subsequent centrifugation method. Only the respective supernatants were used for the injections.

These drug injections were administered to the respective horse at an interval of one week in each case. The first administration was performed at time T24, and the second, third and fourth ones were performed after week 1, after week 2 and after week 3. The drug-containing syringes for the second, third and fourth administration were stored at minus 20° C. until use.

The lameness was checked after 1, 2 and 3 weeks, 3 and 6 months and 1 year and the degree of lameness was rated using a scale of 0-4 (0=no lameness at all, 5=massive lameness) in accordance with the AAEP (American Association of Equine Practitioners).

In all 12 cases, a significant reduction in lameness was found after just 3 weeks. After 6 months and even after one year, all the horses were completely free of symptoms, more particularly free of lameness. During the treatments, no adverse effects at all were found.

Figure 4:
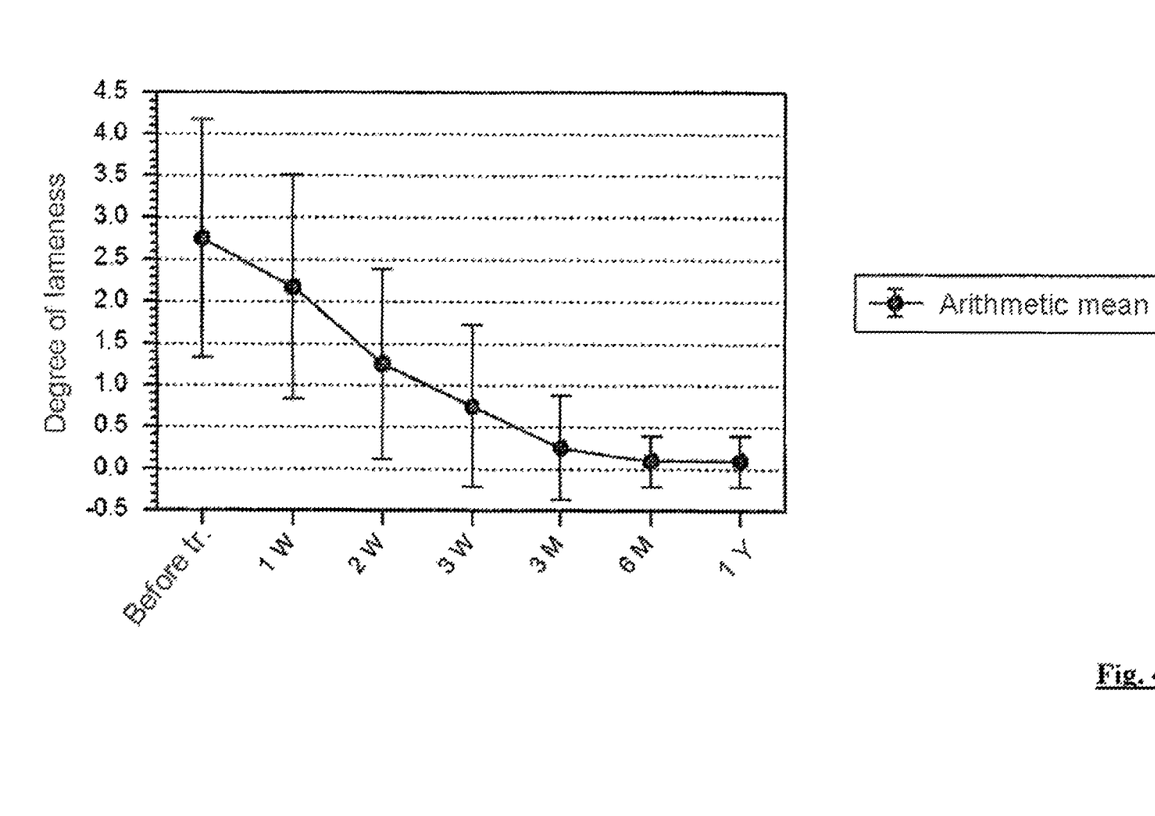
FIG. 4 shows: the graphic representation of the lameness of all horses examined, before and after the treatment according to the invention at the respective re-examination times.

The results of this study are depicted graphically in FIG. 4.

EXAMPLE 3

Production of a Container According to the Invention Containing Gold Particles

The gold particles used were gold powder (particle size 1 μm, Bio-Rad Laboratories, Munich). The gold particles were first sterilized, as recommended by the manufacturer: the required amount of gold particles/gold powder, for example 30 mg, was admixed with 1 ml of 70% strength ethanol, incubated for 10 minutes with light agitation (mixer, vortexer), briefly centrifuged after settling for 1 minute, and subsequently the supernatant was removed. Thereafter, the gold particles were washed three times with 1 ml of sterile double-distilled water in each case. After the last wash procedure with final centrifugation and decanting of the supernatant, the gold particles were resuspended in sterile PBS and adjusted to the desired concentration, for example 60 mg/ml. Under continuous agitation, 10 µl of the gold-particle solution were removed using a pipette and transferred to an S-Monovette-neutral/9 ml (92×16 mm) from Sarstedt (REF 02.1726.001). The monovette was firstly opened in a sterile workbench (screw cap), the 10 µl gold-particle solution was applied to the inner syringe wall, and subsequently it was closed again. The filled monovettes were stored at room temperature until use. For the use when carrying out the method according to the invention, 9 ml of body fluid (e.g. blood) were filled into the thus prepared monovettes and mixed with the gold-particle/PBS solution.

EXAMPLE 4

Drug Efficacy Studies in Humans

As part of a prospective longitudinal study, a total of 9 patients, or 13 joints, suffering from radiologically detected gonarthrosis was treated by a registered physician. The degree of arthrosis was rated grade 3-4 according to the Kellgren-Lawrence scale (Kellgren J. H. and Lawrence J. S.: "Radiological Assessment of Osteo-Arthrosis", Ann. rheum. Dis. (1957), 16, 494-501). All patients each received, at an interval of one week, four intra-articular injections with the autologous serum according to the invention that was firstly treated with gold and subsequently depleted of particles. If there was an intra-articular effusion, this was drained in each case before the injection, the amount drained was documented, and it was frozen in 1 ml aliquots at minus 20° C. for further processing. The clinical result of the treatment was documented before the treatment and 1, 3, 6 and 12 months after the treatment using the validated point assessment system (synonym: score) "KOOS" (Roos E. M., Roos H. P., Lohmander L. S., Ekdahl C., Beynnon B. D.: "Knee Injury and Osteoarthritis Outcome Score (KOOS—development of a self-administered outcome measure", J. Orthop. Sports Phys. Ther. 1998, 28: 88-96). The maximum achievable number of points was 100. The higher the number of points, the better the result achieved. The results are depicted graphically in FIG. 5.

Figure 5:
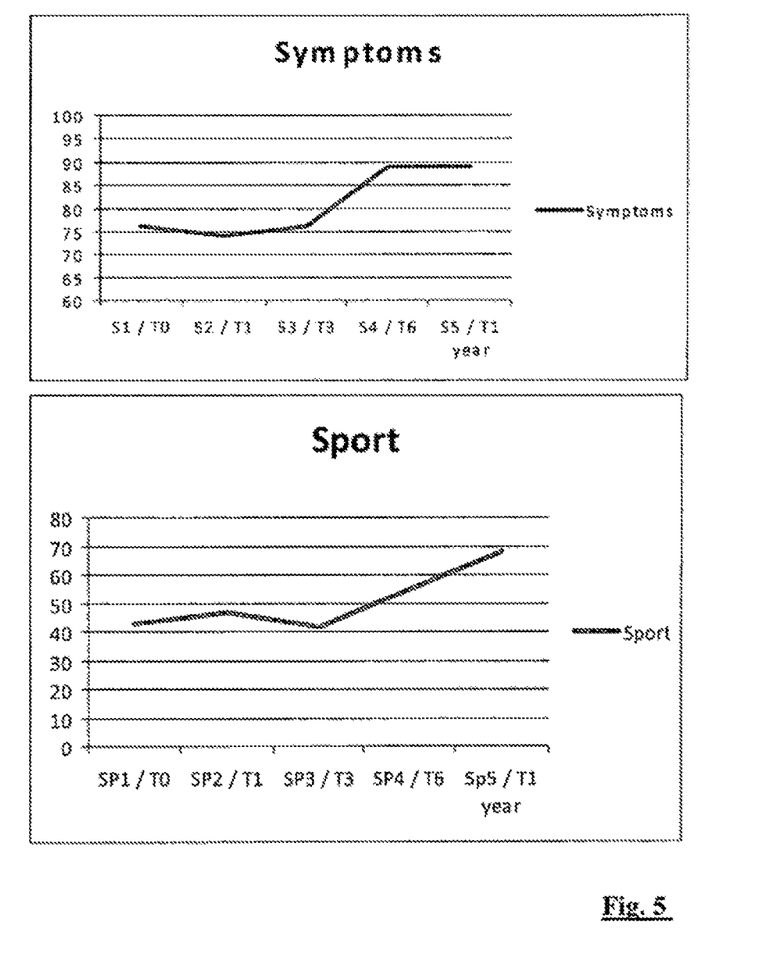
FIG. 5 shows: KOOS score before and after the treatment for patients suffering from gonarthrosis.

The evaluation of the KOOS score with respect to the parameters "symptoms" and "sport activity" showed a distinct improvement in the clinical symptoms after 3 and 6 months (cf. FIG. 5).

In the case of one patient, there was initially considerable effusion. The effusion was drained in each case before the injection treatment, documented with respect to the amount of effusion, and the synovial aspirate was tested with respect to the gelsolin concentration. Since the gelsolin concentration is dependent on the degree of dilution by the effusion, the gelsolin concentration was based on the urea concentration (Kraus et al.: Urea as a Passive Transport Marker for Arthritis Biomarker Studies, ARTHRITIS & RHEUMATISM Vol. 46, No. 2, February 2002, pp. 420-427). The results are depicted graphically in FIG. 6.

Figure 6:
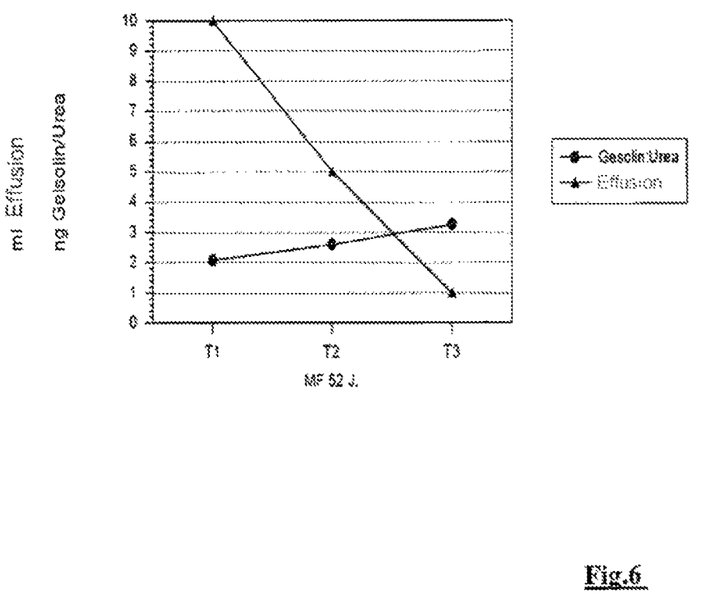
FIG. 6 shows: effusion and gelsolin concentration in the synovial fluid of a patient suffering from gonarthrosis over the course of time: after the 1st (T1), 2nd (T2) and 3rd (T3) injection.

By means of the intra-articular administration of the serum produced according to the invention, i.e. of the serum following incubation with gold particles and subsequent removal of (all) the particles, it was possible to distinctly increase the intra-articular gelsolin concentration (cf. FIG. 6). At the same time, there was a reduction in the amount of effusion (cf. FIG. 6) and, further on, a distinct improvement in the clinical symptoms.

This study thus provides evidence for the use of the drug for the treatment of arthrosis and, in general, of diseases associated with gelsolin deficiency.

EXAMPLE 5

Demonstration of the Chondroprotective Effect of the Drug According to the Invention in an in vitro Cartilage Impact Model The influence of mechanical overloading on the articular cartilage during arthrosis development is sufficiently known. There are also well established and validated in vitro models which test the influence of mechanical load on cartilage-bone explants, for example the model from Huser and Davies (Huser C. A. and Davies M. E.: "Validation of an in vitro single-impact load model of the initiation of osteoarthritis-like changes in articular cartilage", J Orthop Res., April 2006; 24(4): 725-732). A good indicator for commencing cartilage degeneration in such models is the measurement of the proteoglycan content in the culture medium of the cartilage-bone samples tested.

In the course of the investigations which led to the present invention, in an animal-experiment study on the minipig "Göttinger Minipig" involving 6 animals, 4 samples (9 ml) of blood were collected in each case per animal using 9 ml syringes which each contained $10^3$ gold particles, and incubated in accordance with the method according to the invention for 24 h at 37° C. Following the incubation period, the blood samples were centrifuged in the syringe cylinders and, for each syringe (or syringe cylinder), the supernatant was transferred to a fresh/new gold-particle-free syringe cylinder through a sterilizing filter.

In parallel to the collection of the blood samples, cartilage-bone samples were collected from the animals in question under aseptic conditions from the respective femoral heads and cut into blocks of 8×8×10 mm (length/width/height). The cartilage was macroscopically intact in the case of all the explants.

Before use in the impact test, cartilage-bone sample blocks were kept in DMEM medium supplemented with 10% human serum (HS), 100 U/ml penicillin, 100 µg/ml gentamicin and 1.25 U/ml amphotericin B.

On the day of sample collection, the impact test was carried out. For this purpose, a cartilage-bone sample block/explant was arranged in each case under sterile conditions in a cylindrical drop tower composed of polymethyl methacrylate and measuring 33 cm in height and 4 cm axially, at a distance below an impact plunger. The impact plunger was in the form of a cylinder measuring 5 cm in height and 3.94 cm in diameter, and its weight was 493 g. The impact plunger was connected via a thread to the actual impactor disc (impactor unit), which had a weight of 7 g, a height/thickness of 1 cm and a diameter of 0.6 cm.

Impacting was carried out once per cartilage-bone sample block in the drop tower by means of the free fall of the impact plunger containing the impactor disc (impactor) from a height of 15 cm to the sample. Impacting was 0.736 J on a cartilage surface area of 28.3 $mm^2$.

The cartilage-bone sample blocks/explants were divided into 3 groups:
- Explants with no impact treatment="non-impacted controls"="0 controls"
- Explants with impact treatment="impacted controls"="impact controls"
- Explants with impact treatment and subsequent incubation with the protein-enriched blood serum produced according to the invention Following the impact treatment, the treated bone-cartilage preparations and also the 0 controls were washed 3 times with PBS and transferred to 12-well culture plates. Each explant was provided with 3 ml of the respective treatment medium and incubated in an incubator under standardized conditions (37° C., 5% $CO_2$). The culture medium was changed every 72 hours.

The protein-enriched blood serum produced according to the invention was, in the case of the explants, added to the explant group in question on day 0 and day 7.

On day 2, 7 and 14, the proteoglycan content in the culture medium was measured for all the test specimens. For this purpose, the Blyscan Glycosaminoglycan Assay from Biocolor Ltd. (Carrickfergus, UK) was used. The results are depicted in the graph in FIG. 7. The proteoglycan content is specified as the average glycosaminoglycan (GAG) concentration in µg/ml of medium.

Figure 7:
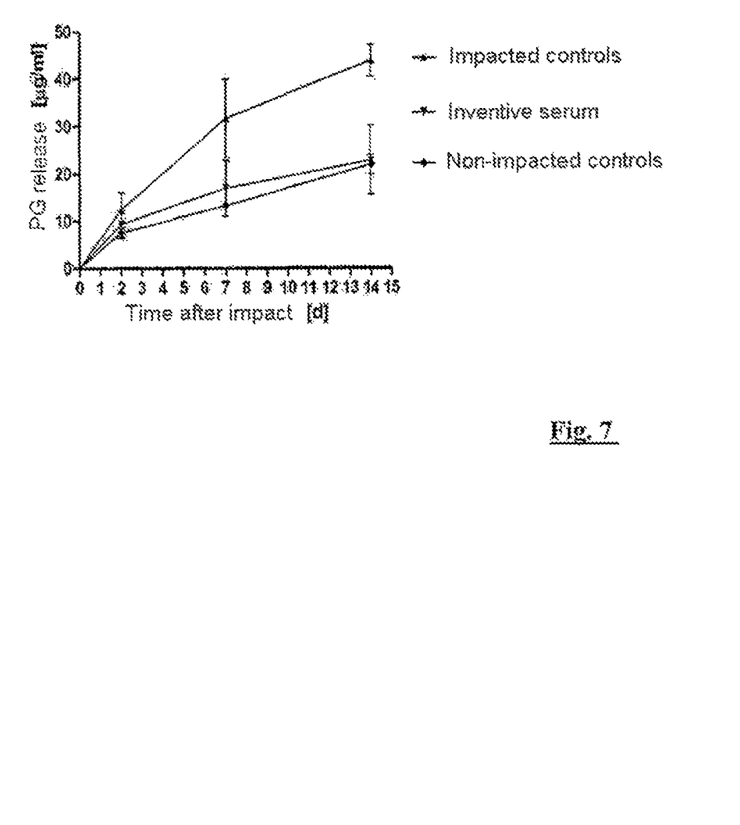
FIG. 7 shows: the proteoglycan release of explants/cartilage-bone preparations after impact treatment.

The analysis of proteoglycan release shows that, in all three groups, viz. the 0 controls and the two impact-treated/impacted explants/cartilage-bone preparations, the proteoglycan amount increases over time.

However, in the case of the explants/cartilage-bone preparations treated with the protein-enriched blood serum produced according to the invention, this rise is only a little stronger than in the case of the non-impacted controls (0 controls), whereas the impact-treated/impacted explants (cartilage-bone preparations) without corresponding serum treatment exhibited a very much higher increase.

This test thus provides evidence for the chondroprotective effect of the drug according to the invention.

TABLE 1

Multiparameter analysis method

| Protein | T0 | Control T24 | StdT T24 | Inv T24 |
|---|---|---|---|---|
| GS | 1990 | 1798 | 1634 | 21 260 |
| IL-4 | 1 | 6 | 7 | 6 |
| IL-10 | 5 | 444 | 438 | 447 |
| IL-13 | 2 | 2 | 2 | 2 |
| IL-1Ra | 1 | 5130 | 5387 | 603 |
| IL-1β | 1 | 808 | 854 | 798 |
| TNF-a | 4 | 78 | 56 | 2444 |
| G-CSF | 6 | 1454 | 1367 | 1890 |
| GM-CSF | 10 | 53 | 45 | 49 |
| IFN-g | 34 | 302 | 312 | 320 |
| SCGF-β | 64 | 800 | 800 | 1000 |
| MIP-1a | 1 | 4500 | 4400 | 4300 |
| MIP-1β | 84 | 2330 | 2100 | 2150 |
| VEGF | 154 | 286 | 290 | 282 |
| IL-18 | 27 | 524 | 520 | 540 |
| MCP-3 | 1 | 56 | 80 | 1019 |
| SDF-a | 64 | 780 | 852 | 993 |
| Basic FGF | 31 | 73 | 79 | 62 |
| GROa | 40 | 2460 | 2800 | 4800 |

While several particular forms of the invention have been illustrated and described, it will be apparent that various modifications can be made without departing from the spirit and scope of the invention. Therefore, it is not intended that the invention be limited except by the following claims. Having described my invention in such terms so as to enable persons skilled in the art to understand the invention, recreate the invention and practice it, and having presently identified the presently preferred embodiments thereof.

I claim:

1. A method of introducing proteins to a patient comprising the steps of:
    collecting a blood serum from a patient;
    mixing the blood serum and gold particles in a container;
    incubating the blood serum and gold particles to produce protein-enriched body fluid serum;
    removing the gold particles from the protein enriched blood serum; and
    administering the protein enriched blood serum to a patient.

2. The method of introducing proteins to a patient of claim 1 wherein the blood serum is autologous or homologous blood to produce a protein enriched blood serum.

3. The method of introducing proteins to a patient of claim 1 wherein the protein enriched blood serum contains gelsolin in an amount which is at least twice the corresponding value for standard blood gelsolin.

4. The method of introducing proteins to a patient of claim 1 wherein the protein enriched blood serum contains gelsolin above the relevant standard blood level for gelsolin and cytokines above the relevant standard blood level for cytokines.

5. The method of introducing proteins to a patient of claim 1 wherein the patient from which the blood serum is extracted is the same patient to whom the blood serum is administered.

6. The method of introducing proteins to a patient of claim 1 wherein the patient from which the blood serum is extracted is not the same patient to whom the blood serum is administered.

7. The method of introducing proteins to a patient of claim 1 wherein the blood serum is autologous or homologous blood, and said blood and protein enriched blood serum have not undergone centrifugation or filtration to remove blood cells prior to administering the protein enriched blood serum to a patient.

8. The method of introducing proteins to a patient of claim 1 wherein the blood serum is autologous or homologous blood, and said blood or protein enriched blood serum have undergone centrifugation or filtration to remove blood cells prior to administering the protein enriched blood serum to a patient.

* * * * *